United States Patent
Asher et al.

[11] Patent Number: 5,984,924
[45] Date of Patent: Nov. 16, 1999

[54] BONE ALIGNMENT SYSTEM HAVING VARIABLE ORIENTATION BONE ANCHORS

[75] Inventors: Marc A. Asher, Leawood, Kans.;
Charles F. Heinig, Anchorage, Va.;
William L. Carson, Columbia, Mo.

[73] Assignee: Isola Implants, Inc., Ware Neck, Va.

[21] Appl. No.: 09/168,980

[22] Filed: Oct. 7, 1998

[51] Int. Cl.⁶ .................................................. A61B 17/70
[52] U.S. Cl. ................................................ 606/61; 606/73
[58] Field of Search .......................... 606/61, 60, 72, 606/73; 623/17

[56] References Cited

U.S. PATENT DOCUMENTS

| | | | |
|---|---|---|---|
| 5,057,111 | 10/1991 | Park | 606/69 |
| 5,147,363 | 9/1992 | Härle | 606/73 |
| 5,190,543 | 3/1993 | Schläpfer | 606/61 |
| 5,234,431 | 8/1993 | Keller | 606/70 |
| 5,368,593 | 11/1994 | Stark | 606/61 |
| 5,474,551 | 12/1995 | Finn et al. | 606/61 |
| 5,486,176 | 1/1996 | Hildebrand et al. | 606/71 |
| 5,501,684 | 3/1996 | Schlapfer et al. | 606/73 |
| 5,569,247 | 10/1996 | Morrison | 606/61 |
| 5,591,166 | 1/1997 | Bernhardt et al. | 606/61 |
| 5,609,592 | 3/1997 | Brumfield et al. | 606/61 |
| 5,647,873 | 7/1997 | Errico et al. | 606/61 |
| 5,688,272 | 11/1997 | Montague et al. | 606/61 |
| 5,688,275 | 11/1997 | Koros et al. | 606/61 |
| 5,716,356 | 2/1998 | Biedermann et al. | 606/61 |
| 5,716,357 | 2/1998 | Rogozinski | 606/61 |
| 5,725,528 | 3/1998 | Errico et al. | 606/61 |
| 5,728,098 | 3/1998 | Sherman et al. | 606/61 |
| 5,735,851 | 4/1998 | Errico et al. | 606/61 |

*Primary Examiner*—Guy V. Tucker
*Assistant Examiner*—Vy Quang Bui
*Attorney, Agent, or Firm*—Sheridan Ross P.C.

[57] ABSTRACT

A bone alignment assembly is disclosed having bone anchor subassemblies for securing to both bones and a bone position retainer, wherein the bone position retainer includes a longitudinal member for maintaining a desired alignment of the bones when the bone anchor assemblies are secured to the bone position retainer. Each of the bone anchor subassemblies includes a shaft and one or more pairs of components (e.g., washers) wherein the components of each pair have mating spherical concave and convex surfaces that can mate together in a plurality of angular positions. When the shaft extends through each of the pairs of mating components, and also through a passageway of the bone position retainer that is sandwiched between the two pairs of mating components, the shaft can be secured at any one of a plurality of orientations relative to the bone position retainer.

31 Claims, 8 Drawing Sheets

BONE ALIGNMENT SYSTEM HAVING VARIABLE ORIENTATION BONE ANCHORS

RELATED FIELD OF INVENTION

The present invention relates to a surgically implanted bone alignment assembly, and in particular, to such an assembly wherein each of the bone anchors included therein can be attached to a bone aligning longitudinal member in any one of a plurality of orientations.

BACKGROUND OF THE INVENTION

Securing and maintaining bones in a preferred alignment may be performed by attaching a plurality of bone anchor subassemblies to one or more bones and subsequently securing the bone anchor subassemblies together in a desired orientation with a bone position retainer, wherein such a bone position retainer includes a "longitudinal member," and in some cases, "connectors" as is known in the art. That is, the longitudinal member connects the bone anchor assemblies together, and (if needed), the connectors are used to secure the bone anchor subassemblies to the longitudinal member. Accordingly, there are at least two criteria that would be desirable to be satisfied when securing bones in a desired alignment using bone anchor subassemblies (also denoted as "bone anchors") and a bone position retainer:

(i) it is desirable to attach each bone anchor to a bone in a manner that will inhibit movement of the anchor relative to the bone. Thus, the orientation of the bone anchor to its attached bone may be dependent on, e.g., the bone configuration, density, and/or fractures therein;

(ii) the bone position retainer must be attached to each bone anchor, and in particular, to an included shaft, in a manner so that the longitudinal member (of the bone position retainer) is oriented to effectively maintain the desired alignment of bones.

In order to satisfy the above criteria, it may be preferable that the shafts of the bone anchors are not parallel to each other and/or not perpendicular to the longitudinal member when they are attached to their respective bones. Moreover, for each bone alignment procedure performed using bone anchors and bone position retainers, the orientations of the shafts relative to one another and the longitudinal member may be substantially unique.

Accordingly, a preferable position of the longitudinal member can be compromised by the various orientations of the bone anchoring shafts, these various orientations due to, e.g., the preferred positions of the anchors when they are secured to the bones. Thus, it would be advantageous to have the ability to firmly secure such bone anchoring shafts to a bone position retainer, wherein the shafts may be at various orientations to the longitudinal member.

SUMMARY OF THE INVENTION

The present invention is a bone alignment assembly that provides bone anchors and a bone position retainer, wherein the bone position retainer includes a "longitudinal member", such as a plate, rod or other elongate biocompatible object, that secures the bone anchors together and thereby induces the bones also secured to the anchors to maintain a desired alignment to one another. Accordingly, each of the bone anchors of the present invention includes a bone attaching portion having, e.g., cancellous threads, hooks and/or clamps for securing the anchor to a bone. The bone attaching portion is secured to (or integral with) one end of a shaft of the bone anchor, and the shaft is additionally secured to the bone position retainer at any one of a plurality of angles between a longitudinal axis of the shaft and the bone position retainer. More precisely, it is an aspect of the present invention that each of the bone anchors can be secured to the bone position retainer at any one of a plurality of angles offset from an axis that is substantially normal to a surface of the bone position retainer through which the bone anchor shaft extends when it is secured to the bone position retainer.

The bone anchors of the present invention can be attached to the longitudinal member by various techniques. In one embodiment, a bone anchor shaft extends through a bore or slot in the longitudinal member as a first step in securing the two together. In another embodiment, a bone anchor shaft extends through a bore or slot provided within a connector of the bone position retainer. However, in all embodiments, it is an aspect of the present invention that the orientation of the bone anchor shaft, relative to the longitudinal member, be securely and fixedly established at a desired orientation as, for example, determined by a surgeon attaching the bone alignment assembly of the present invention to a patient.

It is also an aspect of the present invention, in at least one embodiment, that one or more pairs of mating washers having curved mating surfaces can be used for providing angular variability in the orientation of a bone anchor relative to the bone alignment member. That is, the shaft of each bone anchor is inserted through each of one or more pairs of washers such that the washer pairs allow the shaft to be oriented at various angles relative to the bone position retainer to which the anchor is to be secured. In particular, each such pair of washers have corresponding surfaces that mate together in, for example, a "ball and socket" configuration. Thus, such washer pairs allow substantial angular variation between the bone position retainer and the axis of a bone anchor shaft since the mating surfaces of each of the washer pairs can slide upon one another and mate together at any one of an effectively infinite number of positions. That is, each position corresponds to a different orientation between the bone position retainer and the bone anchor. More precisely, an "inner washer" of each washer pair may have a first surface facing a surface of the bone position retainer, and have a second curved (e.g., spherical) surface upon which a mating "outer washer" of the washer pair may adjustably slide. Accordingly, by providing a pair of such washers on opposing sides of the portion of the bone position retainer through which the shaft of a bone anchor is provided, the various orientations between the shaft and the bone position retainer can be provided by having the outer washer of each washer pair slide across the mating curved surface of its paired inner washer. Thus, since the washer pairs can be tightened together about the bone position retainer, via, e.g., a shaft stop abutting against the outer washer of one washer pair, and a nut threaded onto the shaft that abuts against the outer washer of another washer pair, the orientation of the bone anchor relative to the bone position retainer can be effectively secured in a desired orientation.

Thus, a surgeon can have considerable latitude in positioning the bone position retainer relative to the bone anchors. Accordingly, the bone position retainer can be positioned for enhancing the alignment of the bones, while each bone anchor may be oriented for effectively securing the bone anchors to their bones. Thus, for a bone anchor with a cancellous threaded shaft end for screwing a portion of the shaft into a bone, the surgeon can orient the shaft so that the threads are capable of being screwed into a portion of the bone that will more reliably fix the shaft orientation to the bone (e.g., the shaft is less likely to move within the bone, and the bone is less likely to fracture under stress induced by the bone anchor shaft), and the surgeon can be less concerned about aligning the shaft with the portion of the bone position retainer to which the shaft is to be secured.

Note that in other embodiments of the present invention, an inner washer of a washer pair can be replaced with a curved (spherical) portion of the bone position retainer, wherein this curved portion is capable of mating with the curved surface of an outer washer. That is, the inner washer is, in this embodiment, integral with the bone position retainer. Additionally, it is within the scope of the present invention to replace at least one of the outer washers with an expanded portion of the shaft of a bone anchor, wherein the expanded portion has a curved surface that mates with the curved surface of a paired inner washer. That is, this expanded portion of the shaft includes a curved surface having an extended diameter about an axis for the shaft wherein the curved surface mates with the corresponding surface of an inner washer at any one of a plurality of orientations relative to the bone position retainer.

Thus, the present invention provides a novel, easy to use, and "surgeon friendly" method for inducing a preferred alignment of bones. In particular, by utilizing the apparatus of the present invention, a surgeon can induce an alignment of bones by performing the following steps:

(i) Determining a desired orientation of one or more bones of a patient;

(ii) Determining a position of the bone position retainer that will facilitate the desired orientation of the bones;

(iii) Determining an appropriate type and size of bone anchor for securing each bone to the bone position retainer;

(iv) Securing each bone anchor in a preferred position within a bone; and (v) Securing the bone position retainer to each bone anchor at a desired orientation, wherein for each anchor there is one or more washer pairs (or functional equivalents thereof) for providing mating surfaces that can be tightened together to produce the desired orientation, wherein the friction between the mating surfaces is effective for maintaining the orientation of the bone anchor relative to the bone position retainer.

Moreover, note that it is an aspect of the present invention that the step (v) of securing hereinabove can be performed by tightening a nut onto a threaded portion of the anchor shaft opposite the end of the shaft that secures the bone anchor to a bone. However, other ways of securing the shaft, the washer pairs and the bone position retainer tightly together are also within the scope of the present invention.

Other features and benefits of the present invention will become evident from the detailed description hereinbelow and the accompanying drawings.

BRIEF DESCRIPTION OF THE DRAWINGS

FIG. 5 illustrates another embodiment of the bone alignment 20 of the present invention, wherein a different bone position retainer 24 is utilized. In particular, the bone position retainer is identical with the longitudinal member 24a.

DETAILED DESCRIPTION OF THE PREFERRED EMBODIMENT

Figure 1:
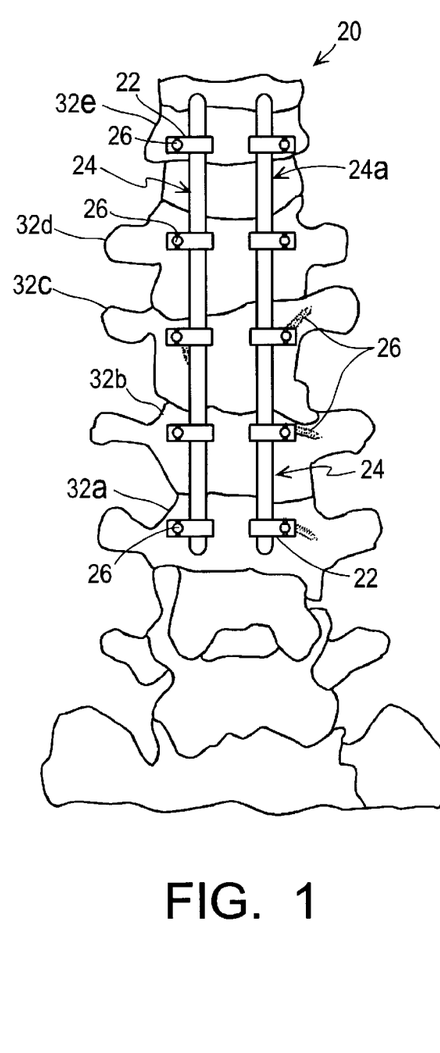
FIG. 1 illustrates the bone alignment assembly 20 of the present invention, wherein the bone anchor subassemblies 26 can be provided at various angles relative to a bone position retainer 24 that connects between the bone anchor subassemblies 26.
Figure 2:
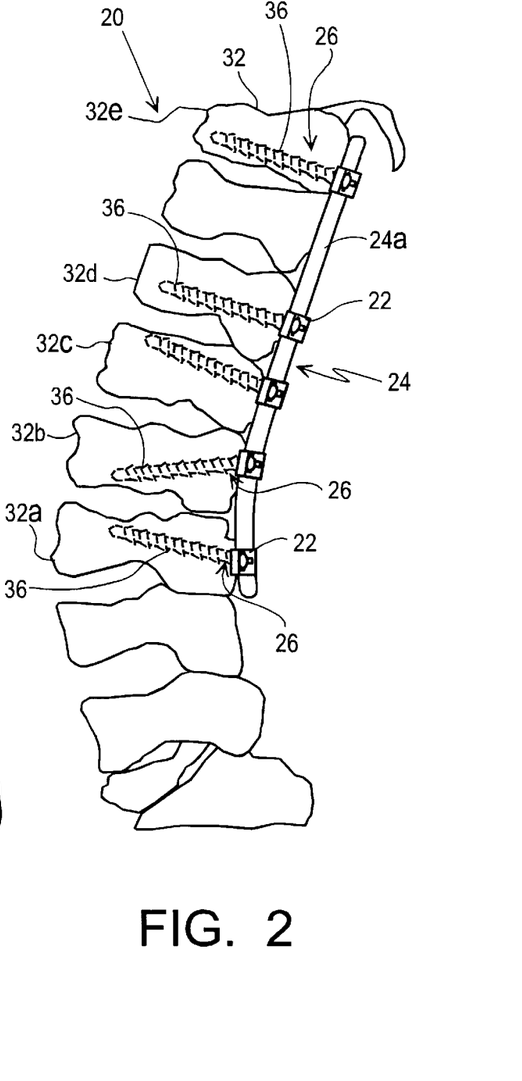
FIG. 2 shows the bone alignment assembly 20 of FIG. 1 from an orthogonal perspective.
Figure 3:
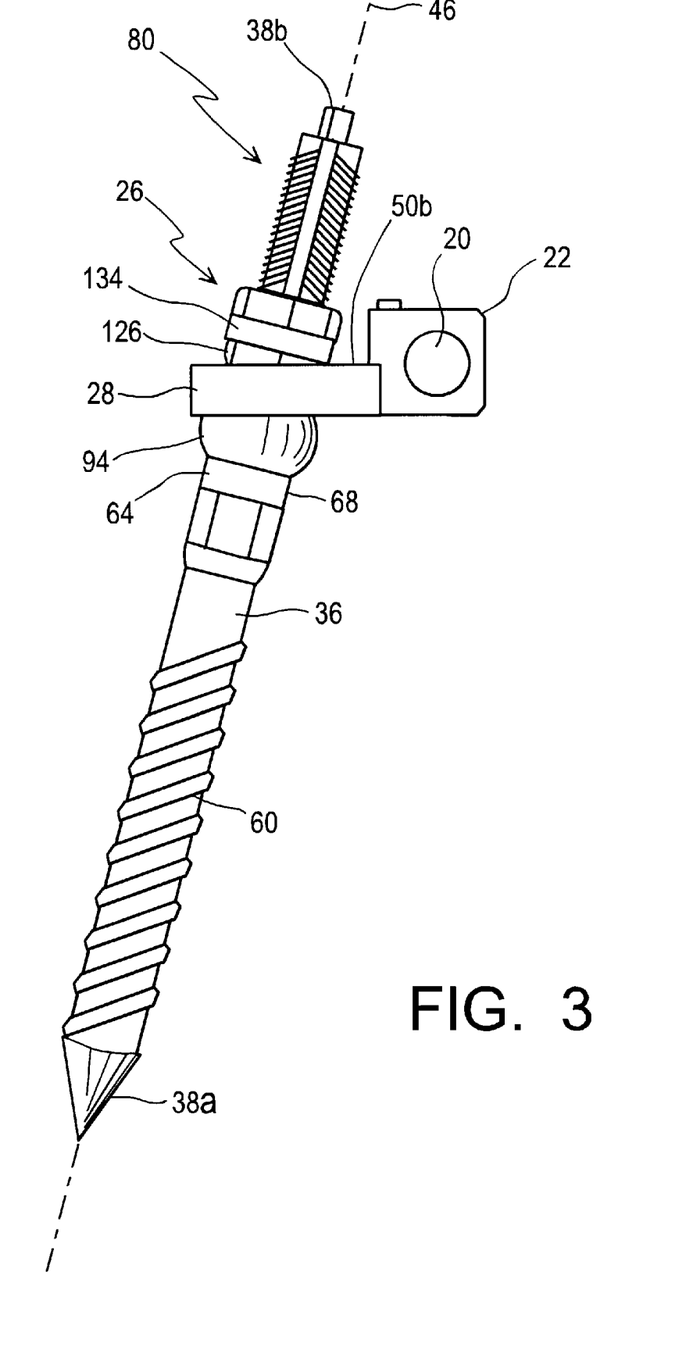
FIG. 3 shows a more detailed view of a bone anchor subassembly 26 (as in FIG. 1).

FIGS. 1, 2 and 3 show a first embodiment of the bone alignment assembly 20 of the present invention. The assembly includes a bone position retainer 24 having a longitudinal member 24a together with at least one bone anchor subassembly 26, but usually used with more than one such subassembly 26 (as shown in FIGS. 1 and 2). Additionally, in the present embodiment, the bone positioning retainer 24 includes connectors 22 for attaching bone anchor subassemblies 26 to the longitudinal member 24a.

Accordingly, the bone alignment assembly 20 allows two or more bones (such as vertebrae 32a, b, c, d and e) to be fixed in their alignment to one another by the present invention. In particular, each bone anchor subassembly 26 includes a shaft 36 extending through the bone position retainer 24 via a bore 28 (FIG. 3). Moreover, the shaft 36 extends into a vertebrae 32 thereby securing the shaft 36 into the vertebrae. Note that as illustrated in FIGS. 1, 2 and 3, the shafts 36 of the bone anchor subassemblies 26 can be angled with respect to the bone position retainer 24. More precisely, each bone anchor subassembly 26 has an axis 46 (FIG. 3) extending the length of the shaft 36, and each such anchor can be aligned so that its corresponding axis 46 is not perpendicular to an adjacent side (50a or 50b) of the connector 22 through which the anchor subassembly 26 extends. In particular, FIGS. 1 and 2 show a plurality of bone anchor subassemblies 26 at various orientations to a bone position retainer 24 (or more precisely, subassemblies 26 are variously oriented with respect to the sides 50a and 50b of the connector 22 pierced by the bone anchor shaft 36).

Figure 4:
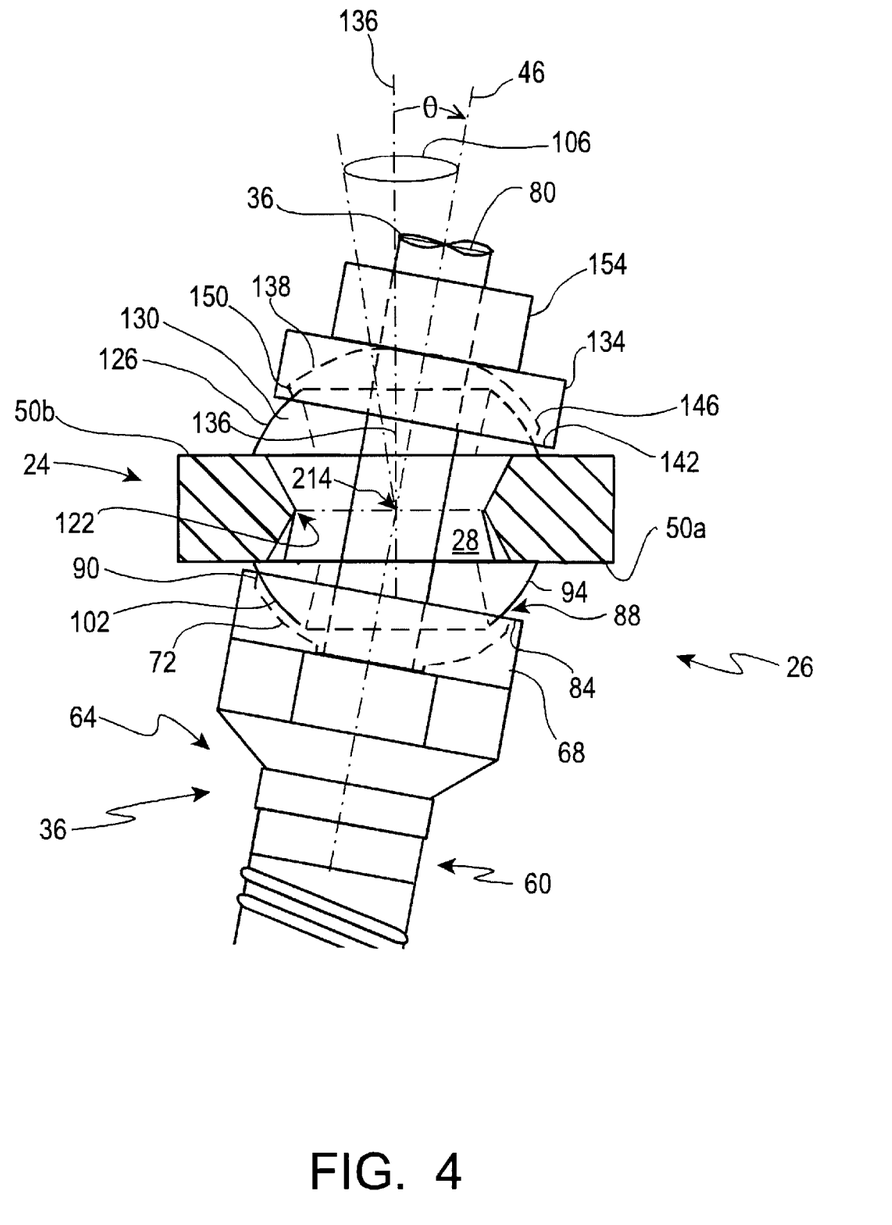
FIG. 4 provides a detailed view of an embodiment of the components of a bone anchor subassembly 26 that allows the bone anchor to be oriented in a plurality of different orientations to the bone position retainer 24.
Figure 6:
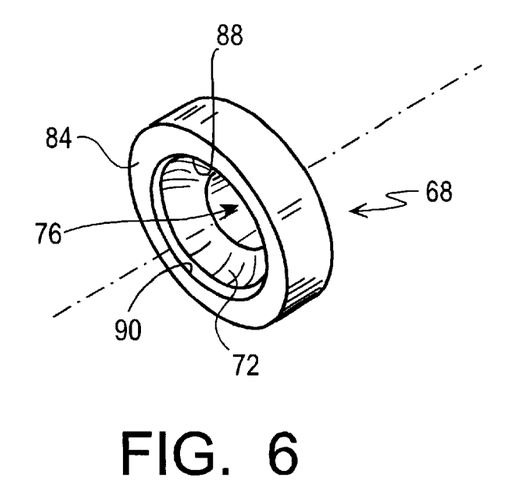
FIG. 6 provides a perspective view of the anterior outside washer 68 having a concave spherical surface 72.
Figure 7:
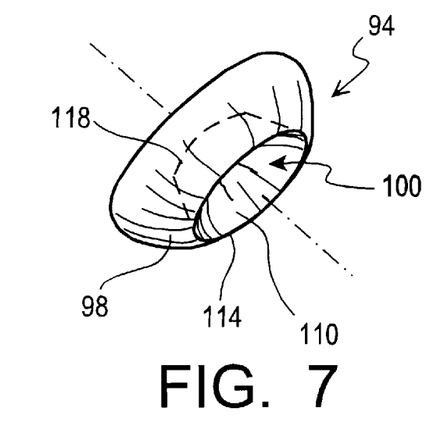
FIG. 7 shows a perspective view of an inner anterior washer 94 having a convex spherical surface 98 which mates with the concave surface 72 (FIG. 6).
Figure 8:
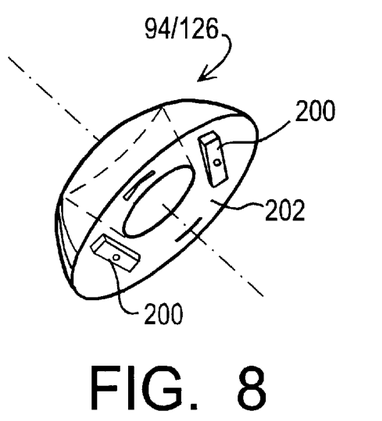
FIG. 8 illustrates an alternative embodiment of the inner anterior washer 94 and/or the inner posterior washer 126, wherein tabs 200 project from the surface 202 that contacts the bone alignment member 24.

Referring now primarily to FIGS. 3 and 4, the subcomponents of a bone anchor subassembly 26 are shown. In the present embodiment, the end 38a of the shaft 36 extending into a vertebrae 32 has cancellous threads 60 for gripping the vertebrae to which it is secured. Additionally, note that there is an expanded portion 64 which, in the present embodiment, is configured as a hexhead that can be used for securely attaching to a tool for threading the threads 60 into a vertebrae 32. Adjacent the hexhead portion 64 and on its side opposite to the bone anchor end 38a is an outer anterior washer 68. The washer 68 is shown in greater detail in FIG. 6. In particular, the washer 68 may have a substantially cylindrical outer profile whereas the inner configuration of the washer 68 facing away from the expanded portion 64 (when the bone anchor assembly 26 is assembled) includes a concave spherical surface 72 having a central opening 76 therethrough such that the portion 80 (FIGS. 3 and 4) of the shaft 36 that is on the side of expanded portion 64 opposite the threads 60 (this portion 80 herein also denoted as machine-threaded post 80, or post 80) can be provided through the opening 76. Additionally, the outer anterior washer 68 includes a lip 84 surrounding the concave surface 72 and providing a relatively sharp edge 88. Between the sharp edge 88 and the concave surface 72 is a wall 90 that is substantially perpendicular to the lip 84. Adjacent and contacting the sharp edge 88 and/or the concave surface 72 is an inner anterior washer 94 (shown in alternative views in FIGS. 7 and 8). The washer 94 has a convex spherical surface 98 with a curvature substantially identical to the concave surface 72. The inner anterior washer 94 also has a central opening 100 through which the machine-threaded post 80 of the shaft 36 can be inserted. Accordingly, as best shown in FIG. 4, when the inner anterior washer 94 is positioned on the shaft 36 between the side 50a of the connector 22, and the outer anterior washer 68, then the sharp edge and/or concave surface 72 and the convex surface 98 mate sufficiently well so that they can be compressed together for assisting in holding the shaft 36 in a desired angle relative to both the bone position retainer 24 and the connector 22. Additionally, note that in the present embodiment, there is a gap 102 (FIG. 4) between these two surfaces. The gap 102 is provided so that when the washers 68 and 94 are compressed together, the sharp edge 88 may be capable of biting or gripping the convex surface 98 for thereby further enhancing the securing of the alignment between the shaft 36, and the bone position retainer 24 (e.g., the connector 22).

The inner anterior washer 94 seats against the connector 22 surface 50a and is aligned with a bore 28 so that the post 80 extending through the bore 28 can also extend through the central opening 100. Note that there is sufficient circumferential contact between the washer 94 and the surface 50a about the bore 28 opening for effectively securing the washer 94 in place with respect to the bore 28. Adjacent the posterior side 50b of the connector 22 is an inner posterior washer 126 which, in the present embodiment, is substantially identical to the inner anterior washer 94. Overlaying the spherical surface 130 (FIG. 4) of the washer 126 is an outer posterior washer 134. Note that in the present embodiment, the washer 134 has features that correspond with the features of the outer anterior washer 68 described hereinabove. In particular, the washer 134 has a concave inner surface 138 (corresponding to the concave surface 72), a lip 142 (corresponding to the lip 84), a wall 146 (corresponding to the wall 90) and a circular relatively sharp edge 150 (corresponding to sharp edge 88). Thus, the inner and outer posterior washers 126 and 134, respectively, mate with one another in a similar fashion and function as do the inner and outer anterior washers 94 and 68, respectively.

Note that, accordingly, the washers 94 and 126 may be manufactured from a material that is more malleable than the washers 68 and 134 so that for each of the outer washers 68 and 134, its sharp edge (88 and 150, respectively) bites into the spherical surface of the adjacent inner washers (94 and 126, respectively) for securing the angular position of the bone anchor assembly 26 relative to bone position retainer 24.

In order to enhance the angular range $\theta$ (FIG. 4) of the axis 46 (e.g. the angular range represented by the circular conic cross-section 106), the inner wall 110 (FIG. 7) of the washer 94 is such that this wall bounds the central opening 100 in an angular fashion so that the diameter of the rim 114 is greater than the diameter of the rim 118.

As an aside, the bore 28 may include angled sidewalls for at least a portion thereof, wherein for a cross-section through the bore (from side 50a to side 50b and perpendicular to at least one of the sides), the bore does not have a uniform width along the axis 136 (FIG. 4); i.e., the bore is tapered. Such angled sidewalls 122 may increase the angular range $\theta$ to which the axis 46 can be angled from a perpendicular axis to one of the sides 50a and 50b.

Overlaying the outer posterior washer 134, is a threaded nut 154 that is capable of mating with threads on the machine-threaded post 80 of the shaft 36. In the present embodiment, the nut 154 is a 5/16" hexhead and the machine threaded post 80 is a 10–32 threaded post, as one skilled in the art will understand. Thus, by threading the nut 154 onto the post 80 and thereby tightening the nut against the outer posterior washer 134, the mating washer pairs (68, 94) and (126, 134) are compressed together for securing the axis 46 of the shaft 36 in a desired position relative to the bone position retainer 24 (or more precisely, the longitudinal member 24a). Note that by using threads and a nut for securing the position of a bone anchor subassembly 26 (more precisely, shaft 36), a substantially continuous range of compressing forces can be applied to compressing the washer pairs between the nut 154 and the expanded portion 64. Thus, small incremental adjustments to the relative positions of the bone position retainer 24 and the bone anchor subassembly 26 can be easily performed by loosening and tightening the nut as needed. However, alternative embodiments for securing a position of the shaft 36 by compressing the washer pairs (68, 94) and (126, 134) (or their functional equivalents) are also within the scope of the present invention. In particular, a rachet component may be used for replacing the nut 154, wherein the rachet component tightens in discrete predetermined amounts.

Thus, it is an aspect of the present invention that when the bone securing end 38a is attached to a bone (e.g. a vertebrae 32), a surgeon can be less concerned with the angle at which the shaft 36 is located relative to the bone, since there is a substantial range of three-dimensional positioning of the bone position retainer 24 that is allowable for subsequently securing it to the shaft 36. In particular, such angular flexibility is provided when securing the shaft 36 to the bone position retainer 24 using the washers 68, 94, 126, 134 and the nut 154. Thus, a surgeon may, for example, secure two bone fastener subassemblies 26 to vertebrae 32a and 32b, respectively, at angles that are substantially chosen to assure that the shafts 36 are firmly secured relative to the bones. Subsequently, the bone alignment assembly 20 may be assembled so that each bone anchor subassembly 26 has the bone position retainer 24 (e.g. the connector 22) sandwiched between the anchor's corresponding pairs of anterior and posterior washers. Accordingly, the surgeon can then have the bone position retainer 24 positioned relative to the bone fastener subassemblies 26 in a more desirable orientation than if the longitudinal axes 46 of the shafts 36 were required to remain fixed at a predetermined angle (e.g., perpendicular) to the bone position retainer 24.

Note that in the current embodiment, the angle θ (FIG. 4) can extend to approximately 15° from the axis 136 that is normal to the sides 50a and 50b. However, larger ranges of angles are also within the scope of the present invention. A dominant limiting factor is the clearance between the machine-threaded post 80 and the angled sidewalls 122. Of course, the range to which the outer washers 68 and 134 can vary over the convex surfaces of their respective inner washers can also be a limiting factor in that the outer washers may extend angularly only so far as to contact one of the surfaces 50a and 50b (as, e.g., shown in FIG. 4). In a more general context, the angle θ is dependent on the following parameters of the bone alignment assembly 20:

(2.1) The conical angles of the inner walls 110 (FIG. 7) and 112 (FIG. 4);

(2.2) The cross-sectional diameter of the machine-threaded post 80;

(2.3) The thickness of the connector 22 in the direction normal to the sides 50a and 50b surrounding the bores 28;

(2.4) A limiting width or diameter of each of the bores 28;

(2.5) The outer extent or radius of the outer washers 68 and 134, and the outer extent or radius of the nut 154;

(2.6) The radius of the central opening through each of the outer washers 68 and 134;

(2.7) The spherical radius of the convex surfaces 98 and 130.

The present invention may have a number of alternative embodiments. Some of these alternative embodiments are described hereinbelow.

Figure 5:
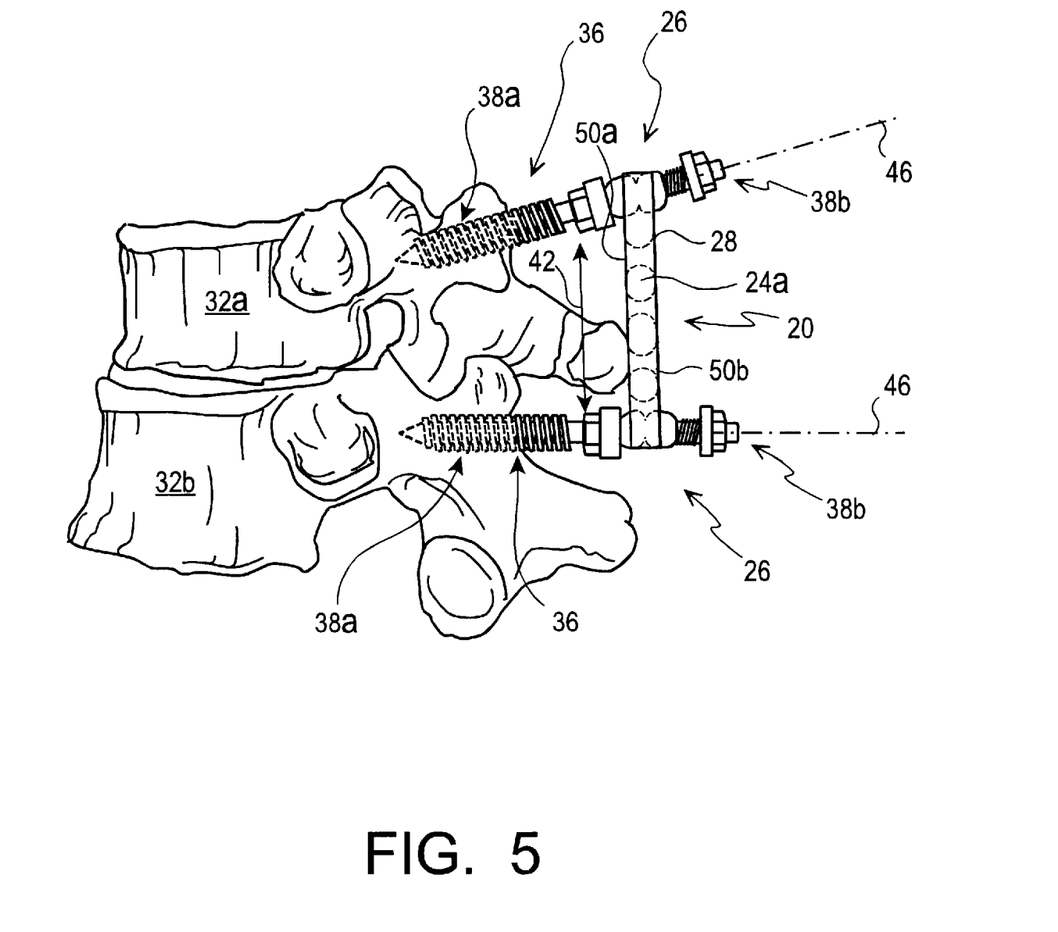

In one embodiment, illustrated in FIG. 5, the bone anchor subassemblies 26 are attached directly to a longitudinal member 24a via bores 28 thereby making the connector 22 unnecessary. Note that the description of the embodiment of FIGS. 1–4 applies equally well here if "longitudinal member 24a" is substituted for "connector 22". Also note that there may be a plurality of the bores 28 along the length (in the direction of double headed arrow 42) of the longitudinal member 24a, wherein the bores pierce the thickness of the longitudinal member.

Figure 9:
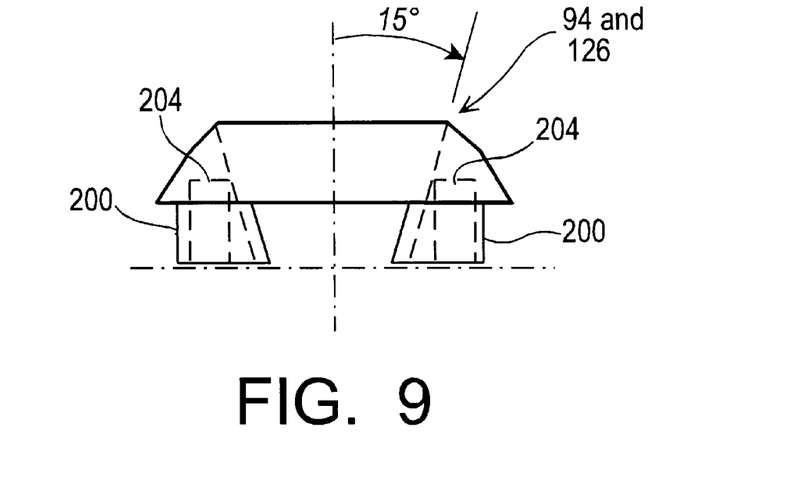
FIG. 9 shows a side view of another embodiment of the inner anterior washer 94 and/or the inner posterior washer 126, wherein there are cylindrical recesses 204 provided within the washer into which a steel pin may be provided for interconnecting the tabs 200 of inner anterior and posterior washers located on opposite sides of the bone position retainer 24.
Figure 10:
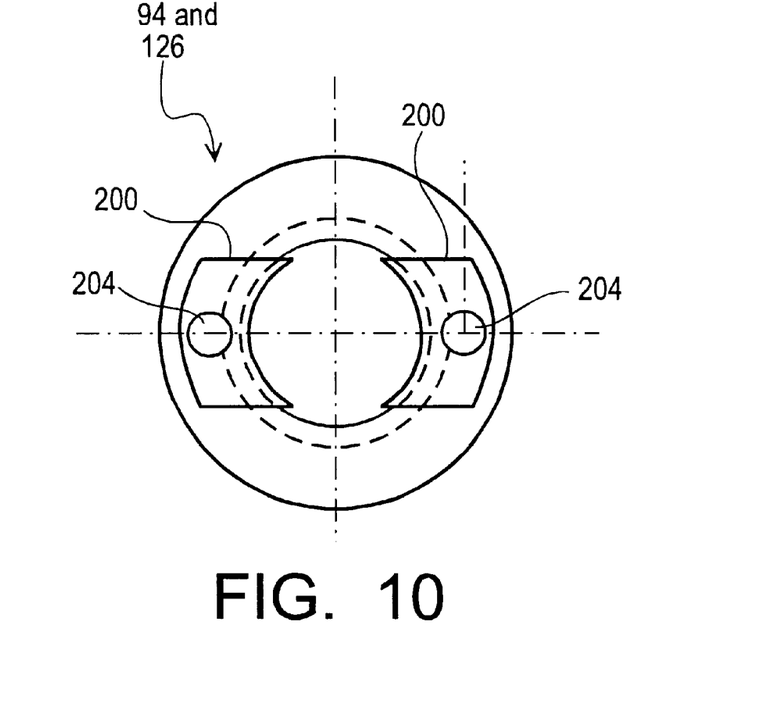
FIG. 10 shows a bottom view of the inner anterior washer 94 and/or the inner posterior washer 126 also shown in FIG. 8.

In another embodiment, the outer anterior washer 68 may be integral with the expanded portion 64 of the shaft 36. Additionally, in some embodiments, the nut 154 and the outer posterior washer 134 may be incorporated into a single component. In some embodiments, either or both of the inner washers 94 and 126 may have tabs projecting from the surface 202 that contacts a side (50a or 50b) of the bone position retainer 24. For example, referring to FIG. 8, one or more tabs 200 may be provided as part of the inner washers. Accordingly, the bone position retainer 24 may be modified to include recesses into which the tabs 200 seat during assembly of a corresponding bone anchor subassembly 26. Moreover, FIGS. 9 and 10 show an alternative embodiment of the inner washers with tabs 200, wherein each tab includes a substantially cylindrical recess 204 into which a steel pin may be provided for interconnecting the two inner washers during assembly of the bone anchor subassembly 26. Note that the use of such tabs 200 may facilitate maintaining alignment of the inner washers during assembly and subsequently during the maintaining of alignments of bones by the present invention.

Figure 11:
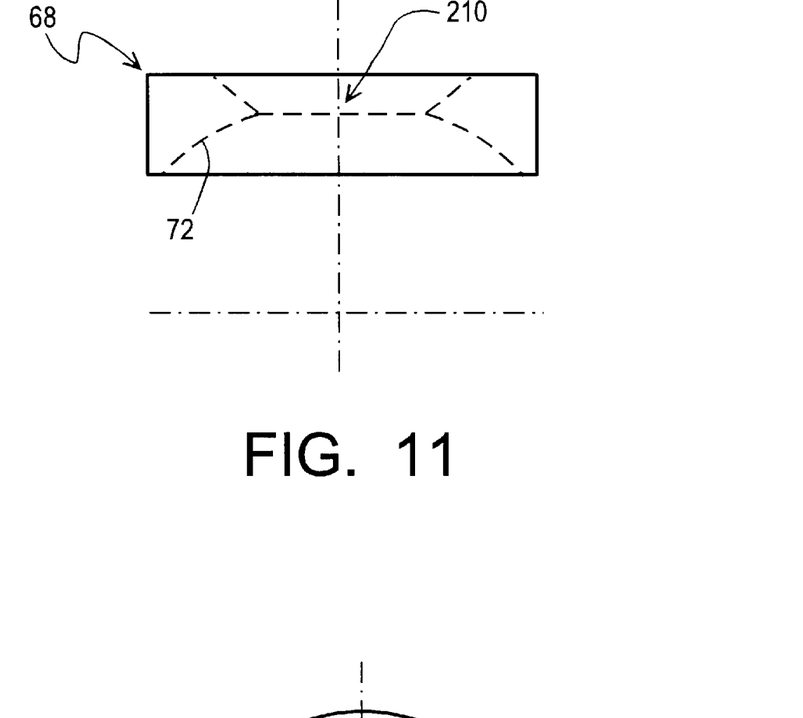
FIG. 11 shows a side view of an alternative embodiment of the outer posterior washer, wherein there is a recess 210 on the opposite side of the washer from the concave inner surface 72 for fitting onto the expanded portion 64 (FIG. 3) of the shaft 36 (FIG. 3).
Figure 12:
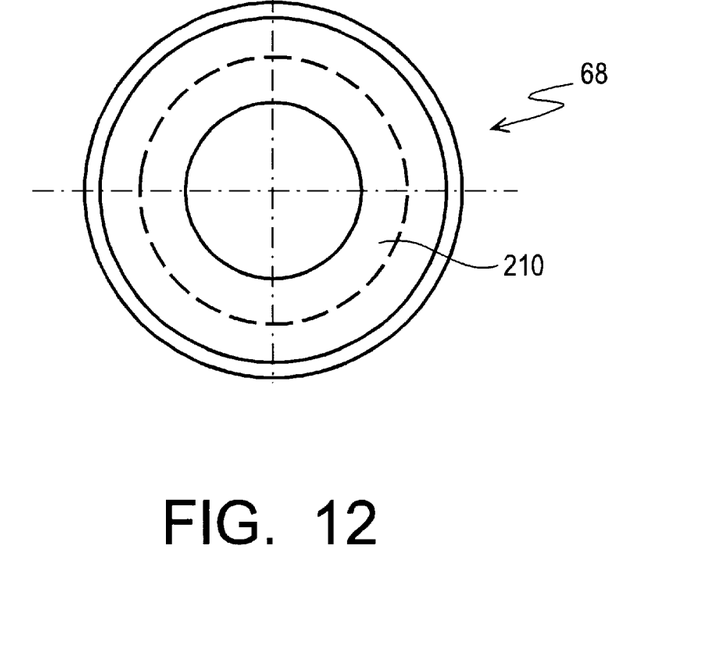
FIG. 12 shows a bottom view of the outer anterior washer 68 embodiment of FIG. 3.

Additionally, in another embodiment of the present invention, one or both of the inner washers 94 and 126 may be replaced by a functionally equivalent spherical portion that is integral with the bone position retainer 24. That is, one or both of the inner washers become part of the bone position retainer 24. In FIGS. 11 and 12, another embodiment of the outer anterior washer 68 is illustrated wherein the washer has a recess 210 on the opposite side from the concave inner surface 72. The recess 210 is a countersink that allows this embodiment of the anterior washer 68 to fit onto and align properly with the expanded portion 64 which is also modified to include a shape for mating with recess 210.

Figure 13:
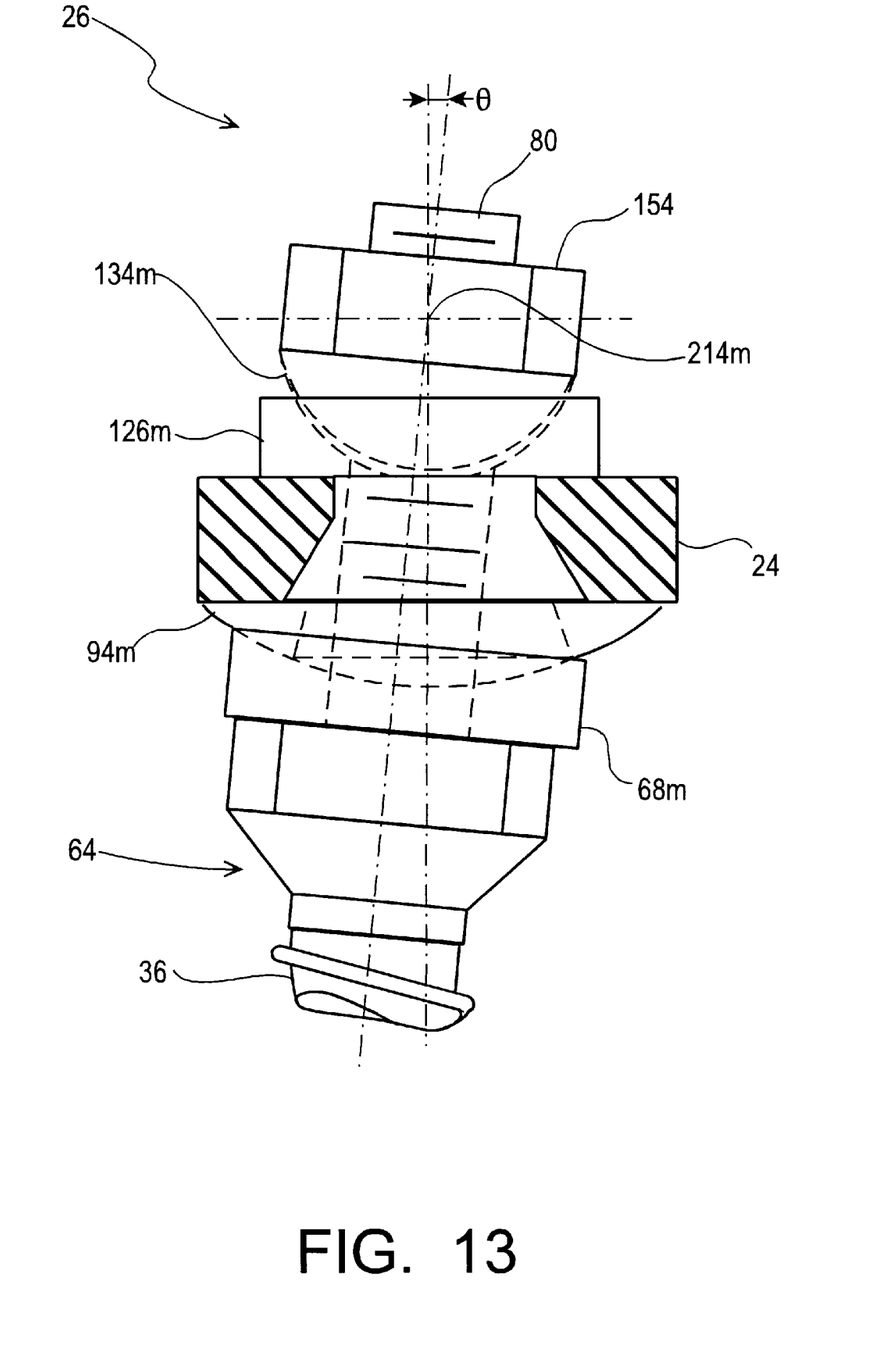
FIG. 13 illustrates an alternative embodiment of the bone anchor subassembly 26.

FIG. 13 illustrates another embodiment of the bone anchor subassembly 26. In this embodiment, components identical to those in previous embodiments are provided with identical labels, and modified components are provided with labels having an "m" attached thereto. Accordingly, the modified components are the washers 68m, 94m, 126m and 134m. In particular, the embodiment of FIG. 13 provides a center at label 214m for the spherical mating surfaces of the modified interior washers 68m and 94m, and the modified posterior washers 126m and 134m. Thus, since the center 214m is to one side of the bone position retainer 24, the spherical curvatures of the mating washers are different. Moreover, the spherical mating surfaces of the washers 126m and 134m are reversed so that the spherical surface of washer 126m is concave and the spherical surface of washer 134m is convex. This configuration creates a different (larger in general) anterior-posterior profile of the bone anchor subassembly, as well as requiring larger diameter, in general, anterior washers.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g. as may be within the skill and knowledge of those in the art, after understanding the present disclosure. It is intended the appended claims be construed to include alternative embodiments to the extent permitted.

What is claimed is:

1. An apparatus for retaining one or more bones in a desired alignment, comprising:

a bone position retainer for maintaining a desired position of a first bone, wherein said bone position retainer includes first and second sides, and having a bore from said first side to said second side;

one or more bone anchors, wherein each of said one or more bone anchors includes (A1) through (A5) as follows:

(A1) a bone anchoring shaft having a shaft axis, said shaft extending through said bore in a direction coincident with the shaft axis, said shaft having a bone contacting portion extending away from said first side, and an opposite portion extending away from said second side, wherein said bone contacting portion secures said shaft to the first bone;

(A2) a first outside component having a surface $S_1$, wherein a curved portion of said surface $S_1$ is one of concave and convex, and wherein said first outside component substantially surrounds a first periphery of said shaft between said first side and said bone contacting portion;

(A3) a first inside component having a surface $S_2$, wherein $S_2$ has a curved surface for mating with said curved portion of $S_1$;

(A4) a second outside component having a surface $S_3$, wherein a curved portion of said surface $S_3$ is one of concave and convex, and wherein said second outside component substantially surrounds a second periphery of said shaft between said second side and an end of said opposite portion, said second periphery being traverse to the shaft axis;

(A5) a second inside component having a surface $S_4$, wherein $S_4$ has a curved surface for mating with said curved portion of $S_3$;

wherein $S_1$ and $S_2$ are capable of being mated together in a plurality of different orientations, and wherein $S_3$ and $S_4$ are also capable of being mated in a plurality of different orientations so that the shaft axis of said shaft can be oriented at a plurality of different orientations relative to the bone position retainer.

2. An apparatus as claimed in claim 1, wherein said bone position retainer includes a longitudinal member for connecting the first bone to a second bone so that the bones are positioned in a desired orientation relative to each other.

3. An apparatus as claimed in claim 2, wherein said longitudinal member connects a first of said bone anchors to a second of said bone anchors, wherein said first bone anchor is securable to said first bone and said second bone anchor is securable to said second bone.

4. An apparatus as claimed in claim 3, wherein said bone position retainer includes a connector for connecting one of said bone anchors to said longitudinal member.

5. An apparatus as claimed in claim 1, wherein said first bone is included in one of a spine and a pelvis.

6. An apparatus as claimed in claim 1, further including first and second compressing components for compressing said first inside and outside components toward said first side, and compressing said second inside and outside components toward said second side, so that said compressing components fix an orientation of the shaft axis of said shaft relative to the bone position retainer.

7. An apparatus as claimed in claim 6, wherein said compressing components include a nut that is being threaded onto threads of said shaft at said opposite portion.

8. An apparatus as claimed in claim 7, wherein said second outside component is connected to said nut prior to said nut being threaded onto said shaft.

9. An apparatus as claimed in claim 6, wherein one of said first and second compressing components includes an enlarged portion of said shaft that abuts against said first outer component.

10. An apparatus as claimed in claim 1, wherein at least one of said surfaces $S_1$ and $S_3$ is spherical.

11. An apparatus as claimed in claim 1, wherein at least one of said first and second inside components is connected to said bone position retainer prior to receiving said shaft through the opening of said at least one inside component.

12. An apparatus as claimed in claim 11, wherein at least one of said first and second inside components is integral with said bone position retainer.

13. An apparatus as claimed in claim 1, wherein said bore includes a tapered wall.

14. An apparatus as claimed in claim 1, wherein at least one of said first inside component and said second inside component has a passageway therethrough for receiving said shaft, wherein said passageway has tapered walls.

15. An apparatus as claimed in claim 1, wherein said shaft is capable of being positioned at any position within a predetermined extent about an axis through said bore, said axis being substantially normal to at least one of said first and second sides of said bone position retainer.

16. An apparatus as claimed in claim 1, wherein said predetermined extent is approximately 15° about a pivot point for said shaft.

17. An apparatus as claimed in claim 1, wherein said first outside component is placed over said one or more bone anchors followed by sequential placement of said first inside component, said bone position retainer, said second inside component and said second outside component.

18. An apparatus as claimed in claim 1, wherein at least one of said first or second outside components is integral with said bone position retainer.

19. An apparatus for retaining one or more bones in a desired alignment, comprising:

a bone position retainer for maintaining a desired position of a first bone, wherein said bone position retainer includes first and second sides, and having a bore from said first side to said second side;

one or more bone anchors, wherein each of said one or more bone anchors includes (A1) through (A5) as follows:

(A1) a bone anchoring shaft having a shaft axis, said shaft extending through said bore in a direction coincident with the shaft axis, said shaft having a bone contacting portion extending away from said first side, and an opposite portion extending away from said second side, wherein said bone contacting portion secures said shaft to the first bone;

(A2) a first outside component having a surface $S_1$, wherein a curved portion of said surface $S_1$ is one of concave and convex, and wherein said first outside component substantially surrounds a first periphery of said shaft between said first side and said bone contacting portion;

(A3) a first inside component having a surface $S_2$, wherein $S_2$ has a curved surface for mating with said curved portion of $S_1$;

(A4) a second outside component having a surface $S_3$, wherein a curved portion of said surface $S_3$ is one of concave and convex, and wherein said second outside component substantially surrounds a second periphery of said shaft between said second side and an end of said opposite portion, said second periphery being traverse to the shaft axis;

(A5) a second inside component having a surface $S_4$, wherein $S_4$ has a curved surface for mating with said curved portion of $S_3$;

wherein $S_1$ and $S_2$ are capable of being mated together in a plurality of different orientations, and wherein $S_3$ and $S_4$ are also capable of being mated in a plurality of different orientations so that the shaft axis of said shaft can be oriented at a plurality of different orientations relative to the bone position retainer, and wherein at least one of said first and second inside components includes a washer that is slidably received on said shaft.

20. An apparatus for retaining one or more bones in a desired alignment, comprising:

a bone position retainer for maintaining a desired position of a first bone, wherein said bone position retainer includes first and second sides, and having a bore from said first side to said second side;

one or more bone anchors, wherein each of said one or more bone anchors includes (A1) through (A5) as follows:
- (A1) a bone anchoring shaft having a shaft axis, said shaft extending through said bore in a direction coincident with the shaft axis, said shaft having a bone contacting portion extending away from said first side, and an opposite portion extending away from said second side, wherein said bone contacting portion secures said shaft to the first bone;
- (A2) a first outside component having a surface $S_1$, wherein a curved portion of said surface $S_1$ is one of concave and convex, and wherein said first outside component substantially surrounds a first periphery of said shaft between said first side and said bone contacting portion;
- (A3) a first inside component having a surface $S_2$, wherein $S_2$ has a curved surface for mating with said curved portion of $S_1$;
- (A4) a second outside component having a surface $S_3$, wherein a curved portion of said surface $S_3$ is one of concave and convex, and wherein said second outside component substantially surrounds a second periphery of said shaft between said second side and an end of said opposite portion, said second periphery being traverse to the shaft axis;
- (A5) a second inside component having a surface $S_4$, wherein $S_4$ has a curved surface for mating with said curved portion of $S_3$;

wherein $S_1$ and $S_2$ are capable of being mated together in a plurality of different orientations, and wherein $S_3$ and $S_4$ are also capable of being mated in a plurality of different orientations so that the shaft axis of said shaft can be oriented at a plurality of different orientations relative to the bone position retainer, and wherein at least one of said outside components includes a washer that is slidably received on said shaft.

21. An apparatus for retaining one or more bones in a desired alignment, comprising:

a bone position retainer for maintaining a desired position of a first bone, wherein said bone position retainer includes first and second sides, and having a bore from said first side to said second side;

one or more bone anchors, wherein each of said one or more bone anchors includes (A1) through (A5) as follows:
- (A1) a bone anchoring shaft having a shaft axis, said shaft extending through said bore in a direction coincident with the shaft axis, said shaft having a bone contacting portion extending away from said first side, and an opposite portion extending away from said second side, wherein said bone contacting portion secures said shaft to the first bone;
- (A2) a first outside component having a surface $S_1$, wherein a curved portion of said surface $S_1$ is one of concave and convex, and wherein said first outside component substantially surrounds a first periphery of said shaft between said first side and said bone contacting portion;
- (A3) a first inside component having a surface $S_2$, wherein $S_2$ has a curved surface for mating with said curved portion of $S_1$;
- (A4) a second outside component having a surface $S_3$, wherein a curved portion of said surface $S_3$ is one of concave and convex, and wherein said second outside component substantially surrounds a second periphery of said shaft between said second side and an end of said opposite portion, said second periphery being traverse to the shaft axis;
- (A5) a second inside component having a surface $S_4$, wherein $S_4$ has a curved surface for mating with said curved portion of $S_3$;

wherein $S_1$ and $S_2$ are capable of being mated together in a plurality of different orientations, and wherein $S_3$ and $S_4$ are also capable of being mated in a plurality of different orientations so that the shaft axis of said shaft can be oriented at a plurality of different orientations relative to the bone position retainer, wherein said at least one of said first and second inside components: (i) includes a tab for mating with said bone position retainer, and (ii) is connected to said bone position retainer prior to receiving said shaft through the opening of said at least one inside component.

22. A method for retaining one or more bones in a desired position, comprising:

securing a bone contacting portion of each of one or more bone anchoring shafts to a corresponding bone, wherein each said shaft has a shaft axis extending from an end of its bone contacting portion to an opposite end of the shaft;

inserting each said shaft through a corresponding passageway of a bone position retainer;

wherein prior to said step of inserting, each of a first outside component and a first inside component are provided about a periphery of said shaft, wherein said first outside and said first inside components have mating curved surfaces $S_1$ and $S_2$, respectively, that are capable of mating in a plurality of different orientations to one another;

providing, on a portion of each said shaft between the corresponding passageway and the opposite end of the shaft, a corresponding tightening component that is capable of tightening together the components of at least one of (A1) and (A2) following:
- (A1) said first outside component and said first inside component provided on said shaft; and
- (A2) a second outside component and a second inside component provided about another periphery of said shaft between said corresponding passageway and said tightening component, wherein said second outside and said second inside components have mating curved surfaces $S_3$ and $S_4$, that are capable of mating in a plurality of different orientations to one another;

moving, for each shaft, at least one of:
- (B1) for said first outside and first inside components about the shaft, said mating surfaces $S_1$ and $S_2$ from one of their mating orientations to another, and
- (B2) for said second outside and second inside components about the shaft, said mating surfaces $S_3$ and $S_4$ from one of their mating orientations to another;

wherein said step of moving positions said bone position retainer in a desired one of a plurality of orientations relative to the one or more bones;

tightening, for each said shaft, said corresponding tightening component toward said corresponding passageway for securing said bone position retainer in a desired orientation relative to the one or more bones.

23. A method as claimed in claim 22, wherein for at least one of said shafts, said corresponding tightening component includes a threaded nut that mates with threads on said shaft.

24. A method as claimed in claim 22, wherein said steps of securing, providing, moving and tightening are interactively performed for different ones of said shafts and different ones of the bones.

25. A method as claimed in claim 22, further including a step of inserting said shaft through an opening in at least one of said first outside component and said first inside component provided about said shaft.

26. A method as claimed in claim 25, wherein for said shaft, one or more of said first outside component, said first inside component, said second outside component, and said second inside component provided about said shaft include a washer.

27. An apparatus for maintaining one or more bones in a desired alignment, comprising:
   a bone position retainer having first and second sides, and having a passageway between said first and second sides;
   a bone anchoring shaft with opposed ends terminating a length of said shaft, wherein said shaft extends through said passageway, said shaft having a bone contacting portion between a first of said ends and said passageway, and said shaft having an opposite portion between a second of said ends and said passageway, wherein said bone contacting portion attaches to a bone;
   a first pair of mating components, $C_1$ and $C_2$, through which said shaft extends between said passageway and said first end, wherein $C_1$ and $C_2$ have, respectively, curved surfaces that are capable of mating together in any one of a plurality of orientations relative to one another;
   a second pair of mating components, $C_3$ and $C_4$, through which said shaft extends between said passageway and said second end, wherein $C_3$ and $C_4$ have, respectively, curved surfaces that are capable of mating together in any one of a plurality of orientations relative to one another;
   a plurality of compression components for compressing together said curved surfaces of $C_1$ and $C_2$, and for compressing together said curved surfaces of $C_3$ and $C_4$, so that an orientation of said shaft is fixed relative to said bone position retainer.

28. An apparatus, as claimed in claim 27, wherein said compression components include first and second enlarged portions attached to said shaft on opposite sides of said passageway, wherein at least one of said first and second enlarged portions is movable toward the other of said enlarged portions for compressing said first and second pairs of mating components therebetween.

29. An apparatus as claimed in claim 27, wherein at least one of said enlarged portions includes a nut that is threaded onto said shaft.

30. An apparatus as claimed in claim 27, wherein said mating curved surfaces of at least one of said first and second pairs include a spherical shape.

31. An apparatus for maintaining one or more bones in a desired alignment, comprising:
   and having a passageway between said first and second sides;
   a bone anchoring shaft with opposed ends terminating a length of said shaft, wherein said shaft extends through said passageway, said shaft having a bone contacting portion between a first of said ends and said passageway, and said shaft having an opposite portion between a second of said ends and said passageway, wherein said bone contacting Portion attaches to a bone;
   a first pair of mating components, $C_1$ and $C_2$, through which said shaft extends between said passageway and said first end, wherein $C_1$ and $C_2$ have, respectively, curved surfaces that are capable of mating together in any one of a plurality of orientations relative to one another;
   a second pair of mating components, $C_3$ and $C_4$, through which said shaft extends between said passageway and said second end, wherein $C_3$ and $C_4$ have, respectively, curved surfaces that are capable of mating together in any one of a plurality of orientations relative to one another;
   a plurality of compression components for compressing together said curved surfaces of $C_1$ and $C_2$, and for compressing together said curved surfaces of $C_3$ and $C_4$, so that an orientation of said shaft is fixed relative to said bone position retainer, wherein at least one component of each of said first and second pairs of components includes a washer that is separable from said shaft and said bone position retainer.

* * * * *